United States Patent [19]

Tan

[11] Patent Number: 5,663,437
[45] Date of Patent: Sep. 2, 1997

[54] 2-(N-BENZOYLIMINO)-4,4-DIAMINOBIPHENYL

[75] Inventor: Loon-Seng Tan, Centerville, Ohio

[73] Assignee: The United States of America as represented by the Secretary of the Air Force, Washington, D.C.

[21] Appl. No.: 605,234

[22] Filed: Feb. 2, 1996

[51] Int. Cl.$^6$ .................... C07C 233/65; C07C 231/02
[52] U.S. Cl. .................... 564/184; 564/142; 564/185
[58] Field of Search .................... 564/142, 184, 564/185

[56] References Cited

PUBLICATIONS

L-S Tan and S.R. Simko, "Aromatic Polyimides Based on an Asymmetrically Benzamide–Pendanted Benzidine", Polymer Preprints, vol. 36, No. 1, Apr. 1995, published Mar. 1, 1995.
Lion et al., Bull.Soc. Chim. Belg., pp. 171–182 (1990).
Kuhlmann et al., J.Med.Chem., pp. 1333–1337 (1981).

*Primary Examiner*—Shailendra Kumar
*Attorney, Agent, or Firm*—Charles E. Bricker; Thomas L. Kundert

[57] ABSTRACT

A new benzidine monomer composition containing an asymmetrically situated benzamide (iminobenzoyl) group:

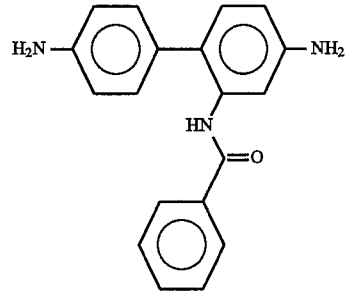

was prepared from the benzolyation reaction of 4,4'-dinitro-2-biphenylamine and benzoyl chloride, followed by catalytic hydrogenation. The compound can be used as a comonomer in the preparation of soluble thermoplastic polyamides, polyimides and other high performance polymers whose preparations require a diamine monomer.

2 Claims, No Drawings

2-(N-BENZOYLIMINO)-4,4'-DIAMINOBIPHENYL

RIGHTS OF THE GOVERNMENT

The invention described herein may be manufactured and used by or for the Government of the United States for all governmental purposes without the payment of any royalty.

BACKGROUND OF THE INVENTION

The present invention relates to a new benzidine-based monomer composition containing a pendant, substituted amide group and a new process for its preparation. This monomer is useful for the preparation of new aromatic polyamides and polyimides for high temperature structural applications.

Rigid-rod polymers are a unique class of thermally stable, aromatic polymers which share the common feature of having a polymer backbone with an all-para geometry and catenation angles of approximately 180 degrees. The only freedom of molecular movement available to this type of structure is the axial rotation, namely, rotations around the carbon-carbon single bonds within the repeat units. Amongst the heterocyclic rigid-rod polymers, the most extensively studied, hitherto, are polybenzoxazole (PBX) family, as represented by polybenzobisthiazoles (PBZT's), polybenzoxazoles (PBO's) and polybenzobisimidazoles (PBI's). The simplest polymers in these families have repeating groups, as follows:

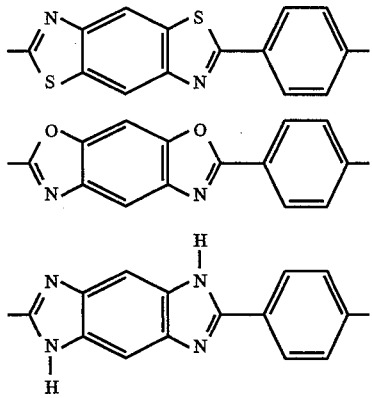

The PBX polymers form lyotropic solutions in polyphosphoric acid, methanesulfonic acid, and Lewis acid/nitroalkane. The exploitation of their lyotropic properties has provided nonmetallic materials in the forms of fibers and films with ultra-high specific strength and moduli.

By their molecular geometry, the combinations of aromatic paradiamines and linear aromatic dianhydrides, such as pyromellitic dianhydride (PMDA), naphthlene carboxylic dianhydride (NCDA) and other related higher homologues, constitute another family of rigid-rod polymers, rigid-rod aromatic polyimides (RRPI's), having aromatic heterocyclic structures. These polymers have repeating units as shown, for example, below:

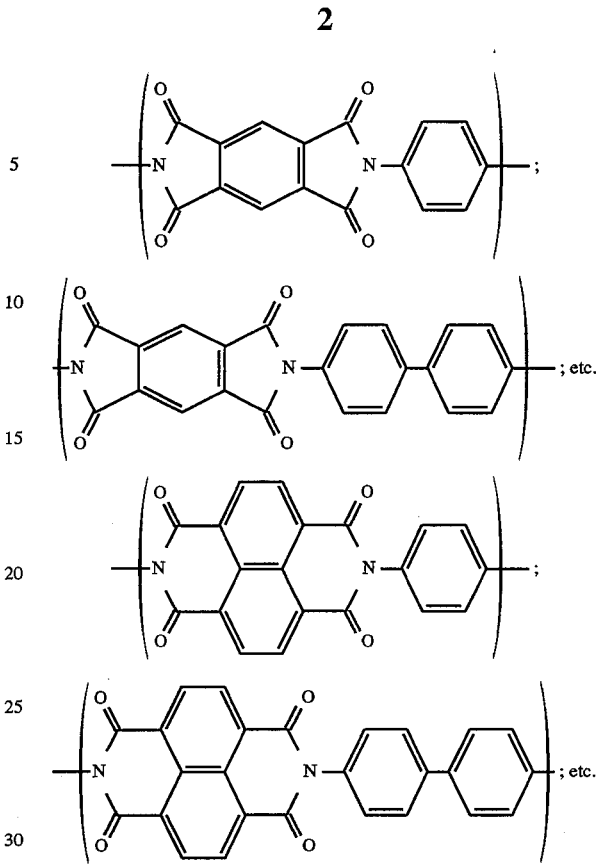

Whereas, as noted previously, PBX polymers form lyotropic solutions in polyphosphoric acid, methanesulfonic acid, and Lewis acid/nitroalkane, RRPI' derived from simple para aromatic diamines show little or no solubility in these acidic solvents. For example, the RRPI derived from PMDA and p-phenylenediamine is only soluble in fuming nitric acid and then only with a substantial degree of polymer degradation.

Because polymer solubility is important in providing more options in the processing and fabrication of RRPI for uses as advanced structural materials and reinforcement component in composites, a common approach to improving their solubilities in organic solvents has been the structural modification of RRPI via pendant chemistry. Thus, extensive backbone substitution with appropriate pendant groups such as, long alkyl chains, phenyl rings, and $SO_3H$, has resulted in PMDA-based RRP's being soluble in solvents ranging from chloroform and toluene to N-methyl-2-pyrrolidinone (NMP) and m-cresol to water and sulfuric acid.

I have prepared a new diamine composition. Its use in the synthesis of a RRPI derived from a symmetrical dianhydride constitutes an alternate route to imparting solubility to RRP's using a simple, asymmetric amide-substituted benzidine.

It is an object of the present invention to provide a new diamine composition.

Other objects and advantages of the present invention will be apparent to those skilled in the art.

SUMMARY OF THE INVENTION

In accordance with the present invention, there is provided the compound 2-(N-benzoylimino)-4,4'-diaminobiphenyl:

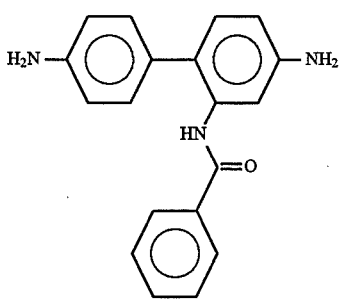

DETAILED DESCRIPTION OF THE INVENTION

The benzidine-based composition of this invention is prepared as shown by the following reaction sequence:

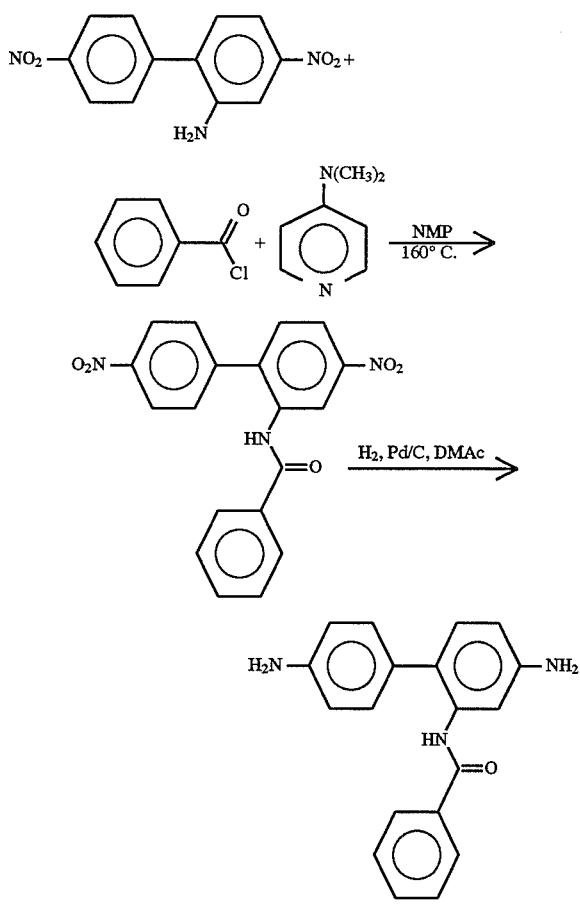

In the first step, 4,4'-dinitro-2-biphenylamine is reacted with benzoyl chloride in the presence of 4-dimethylamine pyridine in N-methyl-2-pyrrolidinone (NMP) to give 2-(N-benzoylimino)-4,4'-dinitrobiphenyl. The hydrogenation of the latter in N,N-dimethylacetamide (DMAc) at room temperature with 10% Pd/C as a catalyst provides the desired 2-(N-benzoylimino)-4,4'-diaminobiphenyl.

The synthesis procedure shown above can be extended to include other alkyl and aromatic acid halides, i.e., alkyl having 6 to 12 carbon atoms and aromatic having 8 to 13 carbon atoms, such as biphenyl, diphenyl ether, naphthenyl, and the like.

The use of 2-(N-benzoylimino)-4,4'-diaminobiphenyl in the synthesis of RRPIs is described in copending application Ser. No. 08/605,231, filed of even date herewith.

The following examples illustrate the invention:

EXAMPLE 1

4,4'-Dinitrobiphenyl-2-Benzamide

A solution of 4,4'-dinitro-2-biphenylamine (12.00 g, 46.29 mmol), 4-dimethylaminopyridine (5.77 g, 47.22 mmol) and N-methyl-2-pyrrolidinone (130ml) was stirred under a nitrogen atmosphere. Benzoyl chloride (9.69 g, 68.92 mmol) was added by dropping funnel at ambient temperature and the mixture heated to 160° C. and maintained at that temperature for 18 h. The resulting solution was poured into 1200 ml ice water with stirring and continued stirring overnight to give a light brown precipitate. The precipitate was filtered out and washed with water (2×100 ml), 5% sodium bicarbonate solution (2×100 ml) and water (4×200 ml) until the filtrate was clear. The crude product was dried under reduced pressure at 138° C. for 24 h to give 4,4'-dinitrobiphenyl-2-benzamide as a light brown powder (16.65 g, 99%), m.p. 242°–244° C.

Anal. Calc. for $C_{19}H_{13}N_3O_5$: C, 62.81; H, 3.61; N, 11.56. Found: C, 61.23; H, 3.57; N, 11.14. Mass Spectrum (EIMS): m/z=363 ($M^+$, 13.2%), 105 (100%). FTIR (KBr): 3209 $cm^{-1}$ (vNH); 1647 $cm^{-1}$ (vCO); 1520 and 1342 $cm^{-1}$ (v$NO_2$).

EXAMPLE 2

4,4'- Diaminobiphenyl-2-Benzamide 4,4'-Dinitrobiphenyl-2-benzamide (16.5 g, 45.4 mmol) was placed in a pressure bottle with 10% palladium on activated carbon (1.95 g, 0.4 mmol), ethyl acetate (70 ml, 14.8 mmol) and N,N-dimethylacetamide (30 ml, 5.9 mmol). The resultant mixture was subjected to catalytic hydrogenation at room temperature at 75.0 to 75.2 psi over a period of 4 h. The reaction mixture was filtered, washed with ethyl acetate until the washings were colorless, then concentrated on a rotary evaporator. The still hot concentrated solution was added dropwise to 1 liter of rapidly stirring water, stirred for 1 h, and the precipitate collected by filtration. The product was again stirred in 1 liter of water for 2 more hours, filtered and dried at 100° C. under reduced pressure for 18 h to give 1.16 g (81%) of a brown solid. The crude product was recrystallized in methylene chloride/hexane and treated with activated charcoal to give a gold precipitate. After filtration the recrystallized product was dried at 100° C. under reduced pressure for 18 h to give 8.3 g gold powder (60% of theoretical yield), m.p.=129°–113° C. Anal. Calc. for $C_{19}H_{17}N_3O$: C, 75.23; H, 5.65; N, 13.85. Found: C, 75.10; H, 5.46; N, 13.50. $^1$H-NMR (chloroform,$d_1$): d3.67 (s, 4H, $NH_2$), d5.30 (w, broad, 1H, NH), d7.4–8.1 (s, 12H, aromatic). FTIR (KBr): 3411 and 3348 $cm^{-1}$ (vNH); 1670 $cm^{-1}$ (vC=O). HPLC (30% THF/70% hexane, normal phase, 2 ml/min, 280 nm): area %=99.9.

Various modifications may be made in the instant invention without departing from the spirit and scope of the appended claims.

I claim:

1. 4,4'-Diaminobiphenyl-2-benzamide.

2. A method for preparing 4,4'-diaminobiphenyl-2-benzamide which consists essentially of the steps of reacting 4,4'-dinitro-2-biphenylamine with benzoyl chloride in the presence of 4-dimethylamine pyridine in N-methyl-2-pyrrolidinone (NMP) to give 2-(N-benzoylimino)-4,4'-dinitrobiphenyl, and hydrogenating said 2-(N-benzoylimino)-4,4:dinitrobiphenyl.

* * * * *